(12) United States Patent
Stopek et al.

(10) Patent No.: US 7,850,982 B2
(45) Date of Patent: Dec. 14, 2010

(54) BIOMATERIAL DRUG DELIVERY AND SURFACE MODIFICATION COMPOSITIONS

(75) Inventors: Joshua Stopek, Yalesville, CT (US); Brian Cuevas, Middletown, CT (US); Joseph Hotter, Middletown, CT (US); Brian Nentwick, Derby, CT (US); Ali Irfan, West Haven, CT (US); Steven Tsai, Stamford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1041 days.

(21) Appl. No.: 11/292,172

(22) Filed: Dec. 1, 2005

(65) Prior Publication Data

US 2006/0193884 A1    Aug. 31, 2006

Related U.S. Application Data

(60) Provisional application No. 60/632,429, filed on Dec. 1, 2004.

(51) Int. Cl.
*A61K 9/00*    (2006.01)

(52) U.S. Cl. .................................................. 424/400

(58) Field of Classification Search ................. None
See application file for complete search history.

(56) References Cited

U.S. PATENT DOCUMENTS

| | | | |
|---|---|---|---|
| 4,047,533 A | 9/1977 | Perciaccante et al. | |
| 4,954,593 A | 9/1990 | Vara et al. | |
| 5,330,768 A | 7/1994 | Park et al. | |
| 5,352,515 A | 10/1994 | Jarrett et al. | |
| 5,442,016 A | 8/1995 | Jarrett et al. | |
| 5,530,074 A | 6/1996 | Jarrett et al. | |
| 5,621,050 A | 4/1997 | Jarrett et al. | |
| 5,716,376 A | 2/1998 | Roby et al. | |
| 5,780,044 A * | 7/1998 | Yewey et al. | 424/426 |
| 6,143,037 A | 11/2000 | Goldstein et al. | |
| 6,177,094 B1 | 1/2001 | Jiang | |
| 6,228,954 B1 | 5/2001 | Kaplan et al. | |
| 6,653,423 B1 | 11/2003 | Yamamoto et al. | |
| 6,706,260 B1 | 3/2004 | Tanaka et al. | |
| 6,805,876 B2 * | 10/2004 | Leong et al. | 424/426 |
| 6,991,804 B2 * | 1/2006 | Helmus et al. | 424/423 |

(Continued)

FOREIGN PATENT DOCUMENTS

EP    0 562 612 A    9/1993

(Continued)

OTHER PUBLICATIONS

Li et al, Morphology and Levonorgestrel Release Behavior of Polycaprolactone/Poly(ethylene oxide)/Polylactide Tri-component Copolymeric Microspheres, Polymers for Advanced Technologies, 2003, 14, 239-244.*

(Continued)

*Primary Examiner*—Michael G Hartley
*Assistant Examiner*—Paul Dickinson

(57) ABSTRACT

Compositions are provided which include a polymer made at least in part from a polyoxyalkylene copolymer, such as a poloxamer. The polymer may be combined with a second component to form a blend or emulsion. The resulting composition may be utilized to form medical devices, drug delivery devices, or coatings for other medical devices.

30 Claims, 1 Drawing Sheet

U.S. PATENT DOCUMENTS

| | | | |
|---|---|---|---|
| 2003/0022242 A1* | 1/2003 | Anderson | 435/7.1 |
| 2003/0157193 A1 | 8/2003 | McDonald et al. | |
| 2005/0175667 A1 | 8/2005 | Carlyle | |
| 2006/0193884 A1 | 8/2006 | Stopek et al. | |
| 2007/0032666 A1 | 2/2007 | Read et al. | |
| 2008/0033106 A1 | 2/2008 | Koroskenyi et al. | |

FOREIGN PATENT DOCUMENTS

| | | |
|---|---|---|
| EP | 055 8965 | 9/1993 |
| EP | 0 752 245 A | 1/1997 |
| WO | WO 2007/133782 A1 | 11/2007 |

OTHER PUBLICATIONS

Ha J C et al: "Poly(ethylene oxide)-poly(propylene oxide)-poly(ethylene oxide) (Pluronic)/poly(sigma-caprolactone) (PCL) amphiphilic block copolymeric nanospheres-I Preperation and characterization" Journal of Controlled Release, Elsevier, Amsterdam, NL, vol. 62, No. 3, Dec. 6, 1999.

International Search Report from Application No. PCT/US07/26003 dated Apr. 16, 2008.

Iwasaki et al., "In vitro and ex vivo blood compatibility study of 2-methacryloyloxyethyl phosphorylcholine (MPC) copolymer-coated hemodialysis hollow fibers", *Journal of Artificial Organs* (2003), 6(4):260-266.

Nakabayashi et al., "Copolymers of 2-methacryloyloxyethyl phosphorylcholine (MPC) as biomaterials", *Bio-Medical Materials and Engineering* (2004), vol. 14, 345-354.

* cited by examiner

BIOMATERIAL DRUG DELIVERY AND SURFACE MODIFICATION COMPOSITIONS

CROSS REFERENCE TO RELATED APPLICATIONS

This application claims priority to U.S. Provisional Patent Application Ser. No. 60/632,429 filed Dec. 1, 2004, the disclosures of which are incorporated herein in their entirety by this reference.

TECHNICAL FIELD

The present disclosure is related to polymer compositions which are particularly useful in the manufacture of medical devices such as sutures, staples, clips, anastomosis rings, bone plates and screws, matrices for the sustained and/or controlled release of pharmaceutically active ingredients, etc. In some embodiments, the polymer compositions may be utilized as coatings for medical devices.

DESCRIPTION OF THE RELATED ART

Coatings for medical devices are also known. Such coatings for medical devices may be utilized to improve surface properties of the device such as, for example, cell and protein adhesion, lubricity, drug delivery, protein or DNA delivery, etc. For sutures, coatings can enhance the suture's handling characteristics, such as surgeon's throw, lubricity, knot run down and/or knot security.

Although present coatings on medical devices perform satisfactorily, there is room for improvement in connection with polymers having enhanced properties for the formation of medical devices and coatings on medical devices.

SUMMARY

Compositions are provided having a polymer made at least in part from a polyoxyalkylene copolymer, such as a poloxamer. In some embodiments the polymer made at least in part from a polyoxyalkylene copolymer may include a bioabsorbable terpolymer.

The polymers made at least in part from a polyoxyalkylene copolymer may be utilized alone or, in some useful embodiments, may be combined with another polymer or oligomer to form a blend or emulsion. In some embodiments the blend or emulsion may include a medicinal agent. The resulting compositions may be utilized to form medical devices, drug delivery devices, or coatings for medical devices.

DETAILED DESCRIPTION

Figure 1:
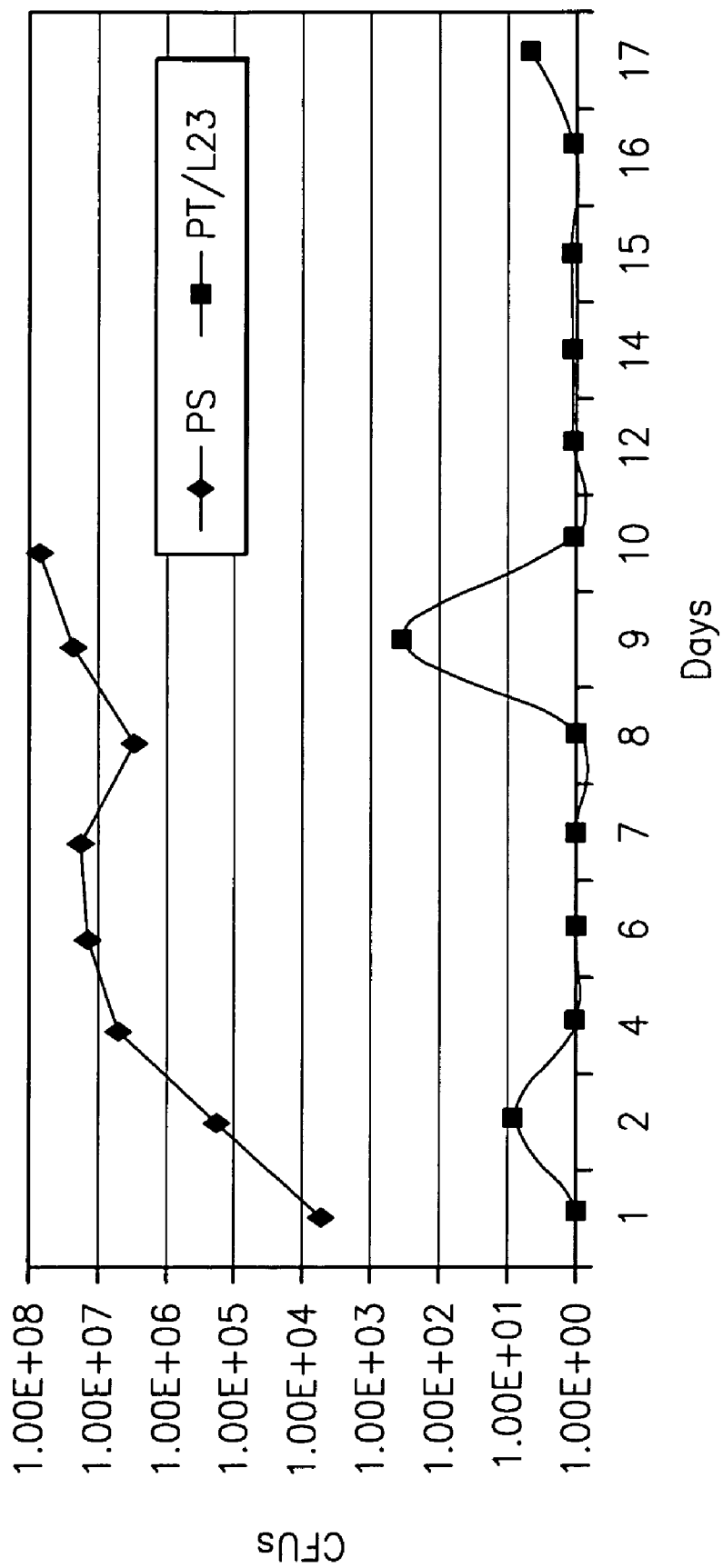
FIG. 1 is a graph comparing bacterial colonization of an untreated POLYSORB® suture with a suture coated with a blend of the present disclosure having triclosan incorporated therein.

The compositions described herein are useful for the formation of medical devices, especially for forming coatings on medical devices and include a blend or emulsion of a first polymer made at least in part from a polyoxyalkylene copolymer and a second component which may be a polymer or oligomer.

The first component in the composition of the present disclosure can be a polymer made at least in part from a polyoxyalkylene block copolymer. Suitable polyoxyalkylene block copolymers include those having an A-B or A-B-A structure wherein "A" is a block made from repeating units of the formula —$O(CH_2)_n$— where n is from 1 to 4 and "B" is a block made from repeating units that are different from the repeating units in the A block and are selected from groups of the formula —$O(CH_2)_n$— where n is from 1 to 4. In particularly useful embodiments, a co-polymer designated as "PEO-PPO-PEO", wherein "PEO" denotes a block of repeating units of the formula —$OCH_2CH_2$— and "PPO" denotes a block of repeating units of the formula —$OCH_2CH_2CH_2$—. Particularly useful are triblock copolymers of the formula $HO(C_2H_4O)_a(C_3H_6O)_b(C_2H_4O)_cH$ wherein a and c are independently from 1-150 units and b ranges from 10-200 units, with the overall molecular weight ranging from 1,000 to 50,000 daltons. Such polyoxyalkylene block copolymers are typically referred to by those skilled in the art as "poloxamers". Particularly useful poloxamers include those where a equals c and b ranges from 10-200 units.

Examples of polyoxyalkylene block copolymers which may be utilized to form the first polymer of the compositions of the present disclosure include poloxamers sold under the trade names PLURONIC® (BASF Corp.) or SYNPERONIC® (ICI). PLURONIC® copolymers are identified by a specific letter-number combination. The alphabetical designation describes the physical form of the product: 'L' for liquids, 'P' for pastes, 'F' for solid forms. The first digit (two digits in a three-digit number) in the numerical designation, multiplied by 300, indicates the approximate molecular weight of the hydrophobic component (propylene oxide). The last digit, when multiplied by 10, indicates the approximate hydrophilic (ethylene oxide) content of the molecule as a percentage by weight. Thus, for example, PLURONIC® F68 is a solid material. The molecular weight of the hydrophobic (propylene oxide) component is approximately 1800 (6×300). The hydrophilic (ethylene oxide) component represents approximately 80% of the molecule by weight (8×10).

Poloxamers can be roughly divided into 3 main categories, all of which can be useful in making the first bioabsorbable polymer of the blends of the present disclosure, namely emulsion forming, micelle forming, and water soluble poloxamers. Various factors which determine poloxamer characteristics and behavior are the molecular weight, PPO:PEO ratio, temperature conditions, concentration, and presence of ionic materials. There is thus a wide range of characteristics in existing commercially available poloxamers which can be exploited in formulating the compositions of the present disclosure, especially where the composition further includes a medicinal agent and is utilized for drug delivery purposes.

In one embodiment, a suitable poloxamer which may be utilized to form the first polymer of the composition of the present disclosure includes a polyoxyethylene-polyoxypropylene triblock copolymer known as poloxamer 188, sold under the trade name PLURONIC® F68 by BASF (Parsippany, N.J.). Other poloxamers which may be utilized in the compositions of the present disclosure include poloxamer 403 (sold as PLURONIC® P123), poloxamer 407 (sold as PLURONIC® P127), poloxamer 402 (sold as PLURONIC® P122), poloxamer 181 (sold as PLURONIC® L61), poloxamer 401 (sold as PLURONIC® L121), poloxamer 185 (sold as PLURONIC® P65), and poloxamer 338 (sold as PLURONIC® F108).

The polyoxyalkylene block copolymers may, in some particularly useful embodiments, be reacted with additional biocompatible, biodegradable monomers to form the first polymer. Suitable monomers which may be reacted with the polyoxyalkylene block copolymers include, for example, alpha-hydroxy acids, lactones, carbonates, esteramides, anhydrides, amino acids, orthoesters, alkylene alkylates, alkylene oxides, biodegradable urethanes, and combinations thereof. Specific examples of suitable biocompatible, biodegradable monomers which may be added to the poloxamer include glycolide, lactide, hydroxybutyric acid, hydroxyvaleric acid, caprolactone, trimethylene carbonate, dimethyl trimethylene carbonate, p-dioxanone, and combinations thereof. These monomers, alone or in combination, can constitute up to about 90% to by total weight of the first polymer component, typically from about 10% to about 75% by total weight of the first polymer component, more typically about 30% to about 65% by total weight of the first polymer component, with the polyoxyalkylene block copolymer making up the balance of the first polymer component. It should, of course, be understood that the other monomers may be reacted first to form a polymer (homopolymer or copolymer (e.g., random, block or the like)) prior to reaction with the polyoxyalkylene block copolymer. Conditions suitable for conducting such reactions are within the purview of one skilled in the art.

In some particularly useful embodiments, in addition to a polyoxyalkylene block copolymer component, the first biocompatible polymer is made at least in part from epsilon-caprolactone, alone or in combination with other monomers. In one such embodiment, a polyoxyalkylene block copolymer is reacted with a ε-caprolactone polymer containing a major amount of epsilon-caprolactone and a minor amount of at least one other copolymerizable monomer or mixture of such monomers. In another embodiment, a polyoxyalkylene block copolymer is reacted with a monomer mixture that includes a major amount of epsilon-caprolactone and a minor amount of at least one other copolymerizable monomer or mixture of such monomers in the presence of a polyhydric alcohol initiator as disclosed in U.S. Pat. No. 6,177,094. The polymerization of these monomers contemplates all of the various types of monomer addition, i.e., simultaneous, sequential, simultaneous followed by sequential, sequential followed by simultaneous, etc. Suitable monomers which can be copolymerized with epsilon-caprolactone include glycolide, lactide, p-dioxanone and trimethylene carbonate.

In one particularly useful embodiment, the first polymer component includes a copolymer composed of about 40% to about 95% (w/w) ε-caprolactone, about 5% to about 15% (w/w) glycolide, and about 5% to about 50% (w/w) poloxamer 188. In some embodiments, the first polymer utilized in forming the composition of the present disclosure may be a bioabsorbable terpolymer composed of about 51% ε-caprolactone, about 9% glycolide, and about 40% poloxamer 188, which is commercially available as POLYTRIBOLATE® (Tyco Healthcare, Mansfield, Mass.).

Methods for forming the first polymer component, including a bioabsorbable terpolymer, are known to those skilled in the art utilizing standard reaction conditions that may be varied depending upon the monomers and poloxamer utilized to form the first bioabsorbable polymer. In some embodiments, the monomers and poloxamer can be combined in the presence of a catalyst such as stannous octoate, sometimes under an inert atmosphere, such as nitrogen gas. In other embodiments it may be desirable to allow the polymerization to occur under a vacuum, e.g., at a pressure less than about 1 Torr. In one particularly useful embodiment, the poloxamer, such as poloxamer 188, may be combined in a reaction vessel with additional monomers such as ε-caprolactone and glycolide in the presence of stannous octoate, heated to a suitable temperature ranging from about 170° C. to about 185° C., typically from about 175° C. to about 180° C., such as about 178° C. The monomers may be allowed to polymerize for a suitable period of time which can range from about 4 hours to about 6 hours, typically from about 4.25 hours to about 4.75 hours. After this time, the molten bioabsorbable polymer may be extruded. While not necessary, in some embodiments the bioabsorbable polymer may be subjected to a further heat treatment by heating to a temperature ranging from about 100° C. to about 120° C., typically from about 107° C. to about 113° C., for a period of time ranging from about 25 hours to about 35 hours, typically from about 28 hours to about 32 hours. In some cases it may be desirable for this second heat treatment to occur under a vacuum, at a pressure typically less than about 1 Torr.

In some embodiments, the first polymer component may be utilized alone in an effective antimicrobial amount to form a medical device or a coating for a substrate. An "effective antimicrobial amount" of a given component is an amount at which the component hinders the growth of bacteria associated with infections, and promotes the healing of a wound. Such coatings can prevent bacterial colonization on surfaces at levels of clinical infection, in some cases as much as 14 days or more.

However, the compositions of the present disclosure typically include a first polymer component made at least in part from a polyoxyalkylene copolymer combined with a second polymer or oligomer. Suitable polymers and/or oligomers for use as the second component include lactides, glycolides, lactide-co-glycolides, lactic acids, lactones, glycolic acids, carbonates, dioxanones, esteramides, anhydrides, amino acids, orthoesters, dioxepanones, alkylene alkylates, alkylene oxides, absorbable urethanes, absorbable nylons, and homopolymers and copolymers thereof.

In some embodiments, the second component may be derived from two or more monomers, including polyethylene glycol-polypropylene glycol (PEG-PPG), polystyrene, n-vinyl pyrrolidine, n-vinyl pyridine, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorocholine. In some particularly useful embodiments, the second component may be a copolymer of epsilon caprolactone and glycolide having approximately 85-95% (w/w) ε-caprolactone and 5-15% (w/w) glycolide.

In some embodiments, the first polymer component made at least in part from a polyoxyalkylene copolymer may be combined with the second component to form a blend. In other embodiments, the first polymer component made at least in part from a polyoxyalkylene copolymer may be combined with the second component to form an emulsion or suspension.

In some embodiments, the present compositions also include a fatty acid component that contains a fatty acid or a fatty acid salt or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to 22 carbon atoms, and mixtures thereof. Fatty acid salts including the calcium, magnesium, barium, aluminum, and zinc salts of stearic, palmitic and oleic acids may be useful in some embodiments of the present disclosure. Particularly useful salts include commercial "food grade" calcium stearate which consists of a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions of the present disclosure include calcium, magnesium, aluminum, barium, or zinc stearoyl lactylate; calcium, magnesium, aluminum, barium, or zinc palmityl lactylate; calcium, magnesium, aluminum, barium, or zinc olelyl lactylate; with calcium stearoyl-2-lactylate (such as the calcium stearoyl-2-lactylate commercially available under the tradename VERV from American Ingredients Co., Kansas City, Mo.) being particularly useful. Other fatty acid ester salts which may be utilized include those selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

In some embodiments it may be desirable to include a wax in the composition of the present disclosure. Suitable waxes which may be utilized include polyethylene wax, ethylene copolymer wax, halogenated hydrocarbon waxes, hydrogenated vegetable oil, beeswax, caranuba wax, paraffin, microcrystalline wax, candelillia, spermacetic wax, and mixtures thereof.

In other embodiments, omega-6 fatty acids, including arachidonic acid, may be added to the compositions of the present disclosure.

In yet additional embodiments, phospholipids may be added to the compositions of the present disclosure. Suitable phospholipids include, but are not limited to, phosphatidylcholine (PC), mono-acyl phosphatidylcholine (MAPC), diacyl phosphatidylcholine (DAPC), phosphatidylserine (PS), phosphatidylethanolamine (PE), phosphatidylinositol (PI), phosphatidylglycerol (PG), plasmalogen, sphingomyelin, ceramide, ciliatin, polymers having phospholipid groups, and derivatives thereof. In some embodiments copolymers having phosphorylcholine groups may be added to the compositions of the present disclosure, such as copolymers of 2-methacryloyloxyethyl phosphorylcholine with other monomers, including methacrylates such as butyl methacrylate, benzyl methacrylate, methacryloyloxyethyl phenylcarbamate, and phenyl methacryloyloxyethyl carbamate.

The amount of the first polymer made at least in part from a polyoxyalkylene copolymer in the compositions of the present disclosure can range from about 2% by weight to about 100% by weight, typically from about 5% by weight to about 80% by weight, more typically from about 10% by weight to about 50% by weight of the bioabsorbable composition. The amount of second component in the blends or emulsions of the present disclosure may be up to about 98% by weight and typically ranges from about 20% by weight to about 95% by weight, more typically from about 50% by weight to about 90% by weight of the composition of the present disclosure.

Where utilized, the amount of fatty acid component can range in an amount from about 5 percent to about 50 percent by weight of the total composition. Typically, the fatty acid component may be present in an amount from about 10 percent to about 20 percent by weight of the total composition.

In other embodiments, the polymer components utilized to form the blend or emulsion of the present disclosure may be added separately to coat a substrate. In such a case, the substrate may be first coated with either of the components, i.e., the first polymer made at least in part from a polyoxyalkylene copolymer or the second component, followed by application of the other. Thus, in one useful embodiment, the substrate may be first coated using a first composition containing a bioabsorbable polymer comprising ϵ-caprolactone, glycolide, and optionally a fatty acid component, such as a salt of a fatty acid ester (e.g., calcium stearoyl-2-lactylate). After the first coating has been applied, a second composition can be used to apply the other bioabsorbable polymer, such as a copolymer of ϵ-caprolactone, glycolide, and poloxamer 188, (e.g., the commercially available POLYTRIBOLATE® copolymer). Depending on the conditions of application, the two components can be applied as separate coatings or the two components can be sequentially applied and allowed to combine with each other on the surface of the substrate such as, for example, by controlling the rate of evaporation of the solvent.

In some embodiments, the composition of the present disclosure may also include one or more medicinal agents which are released from the bioabsorbable blend in vivo. As used herein, "medicinal agent" is used in its broadest sense and includes any substance or mixture of substances that have clinical use. Consequently, medicinal agents may or may not have pharmacological activity per se, e.g., a dye. Examples of classes of medicinal agents which may be combined or mixed into the bioabsorbable blend of the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, steroids, polysaccharides, and enzymes. It is also intended that combinations of medicinal agents may be used.

Suitable antimicrobial agents which may be included as a medicinal agent in the bioabsorbable blend of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicinal agent in the blend or emulsion of the present disclosure.

Other medicinal agents which may be included as a medicinal agent in the composition of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antifungals; antivirals; anticoagulants; anticonvulsants; antidepressants; antihistamines; and immunological agents.

Other examples of suitable medicinal agents which may be included in the composition, such as a bioabsorbable blend or emulsion of the present disclosure, include viruses and cells, peptides (e.g., luteinizing-hormone-releasing-hormone analogues, such as goserelin and exendin) and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, gonadotropins (e.g., FSH, LH, CG, etc.), hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

The amount of medicinal agent present will depend upon the particular medicinal agent chosen, but typically the amount used will be in the range of 0.01 to 10% by weight of the composition.

The compositions of the present disclosure can be prepared using any technique within the purview of those skilled in the art. Where the polymers utilized to form the composition are both soluble in the same solvent, the appropriate amounts of each polymer can be dissolved in the solvent and applied to the medical device as a solution. Upon evaporation of the solvent, a coating of the blend will remain on the medical device. Some blends may be obtained with ordinary mixing. In other embodiments, especially where the bioabsorbable blend is to be utilized to deliver a medicinal agent, it may be desirable to mix the medicinal agent in the composition by processes such as ball mill, disc mill, sand mill, attritor, rotor stator mixer, ultrasonication, etc. In other embodiments, the two polymers can be melt blended and used to form or coat a medical device. Other methods for making and using the present blends will be readily apparent to those skilled in the art.

Alternatively, where the two components of the composition of the present disclosure are not completely miscible with each other or the solvents utilized to form the compositions, emulsions may be formed and utilized by any means known to those skilled in the art to form medical devices including drug delivery devices or coatings for medical devices.

When a medicinal agent is used, the medicinal agent may be placed in solution, the composition of the present disclosure may be placed in a separate solution, and the two combined to form an emulsion or suspension. Biocompatible dispersing agents in the form of surfactants, emulsifiers, or stablilizers may be added to the blend to assist in dispersion of the medicinal agent throughout the composition of the present disclosure.

Adjuvants may be added to stabilize or preserve the compositions described above. Such adjuvants include nonionic surfactants which include alcohol ethoxylates, glycerol esters, polyoxyethylene esters, and glycol esters of fatty acids. Preferable nonionic surfactants are glycerol esters of stearic, oleic, and/or lauric acid as well as ethylene and/or diethylene glycol esters of fatty acids.

The compositions described herein are non-toxic. Depending on its particular physical and properties (to a large extent influenced by the nature of the polymers from which it is prepared), the blends and/or emulsions herein can be used in the fabrication in whole or in part of a variety of implantable medical devices and prostheses, e.g., clips, staples, sutures, suture coatings, etc. Applied to a suture, a coating composition containing the composition herein results in a suture having suitable lubricity, knot tiedown, and knot security characteristics.

Where the composition of the present disclosure is used to form a medical device, the devices may be made by injection molding the blend at temperatures and pressures known to those skilled in the art. Typically, the feed for the injection molding apparatus is a melt blend of the two polymer components in pellet form. The components should be quite dry when being injection molded in order to avoid hydrolytic degradation during processing. After molding, the surgical devices can be packaged and sterilized by conventional procedures. It may be desirable to anneal the devices to remove residual stresses and strains, to stabilize the shape of the device, and to reduce or eliminate defects in the piece. Annealing typically comprises reheating the medical device to above its glass transition temperature where chain mobility is greatest, and then slowly and gradually cooling the device to avoid reintroducing. Procedures, conditions and apparatus for annealing polymeric structures are well known in the art.

Where the composition of the present disclosure is used as an absorbable coating for a medical device, the coating may be formed using any known technique such as, for example, extrusion, molding and/or solvent casting. The composition can be used alone, blended with absorbable compositions, or blended with non-absorbable components. A wide variety of surgical articles can be coated with the compositions herein. These include, but are not limited to, clips and other fasteners, staples, sutures, pins, screws, prosthetic device, wound dressings, drug delivery devices, anastomosis rings, and other implantable devices. Fibers coated with the present compositions can be knitted or woven with other fibers, either absorbable or nonabsorbable to form meshes or fabrics.

In one embodiment the composition of the present disclosure may be applied as a coating by dissolving it in a solvent which is a non-solvent for any polymeric device to which the coating is to be applied. The solution containing the composition of the present disclosure may then be applied to a medical device by dipping the medical device into the solution, by passing the medical device past a brush or other applicator, or by spraying the solution onto the surface of the medical device. Suitable solvents for use in dissolving the composition of the present disclosure include, but are not limited to, volatile solvents such as methylene chloride and acetone. The medical device wetted with the coating solution may then be subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

Where applied in solution, the amount of solvent utilized can range from about 85% to about 99% by weight, typically from about 90% to about 98% by weight of the solution utilized to apply the composition of the present disclosure, including the blend or emulsion described above, and any additional medicinal agents or adjuvants. In some embodiments the solvent may be present at about 95% by weight of the solution utilized to apply the composition of the present disclosure.

While the above description focuses on the use of a blend or emulsion as a medical device, drug delivery device, or coating composition in accordance with the present disclosure, optionally in combination with medicinal agents or adjuvants, similar methods and procedures may be utilized where the composition of the present disclosure includes the polymer made at least in part from a polyoxyalkylene copolymer in combination with a medicinal agent or adjuvant, without the addition of a second component, which can be a polymer or oligomer. As would be readily apparent to one skilled in the art, one could utilize the same or similar solvents, processing conditions, etc. in utilizing a polymer made at least in part from a polyoxyalkylene copolymer as the composition of the present disclosure.

While the composition herein can be applied to any type of medical device, it may be especially useful as a coating for a suture. The amount of composition applied to a suture will vary depending upon the structure of the suture, e.g., monofilament or multifilament, the size of the suture and its composition. For multifilament sutures, the number of filaments and the tightness of the braid or twist may also influence the amount of coating.

The coating may be applied to both monofilament and multifilament braided sutures which may, in some embodiments, also be bioabsorbable. Suitable bioabsorbable monomers and polymers utilized for the sutures, including bioabsorbable braided sutures, include lactide, glycolide, trimethylcarbonate, ε-caprolactone, caprolactam, polyesters, nylons, etc. The coating can typically be present in an amount ranging from about 0.5 to about 15% (w/w) of the base suture substrate, more typically from about 1 to about 5% (w/w) of the base suture substrate. The thickness of the coating will depend on a number of factors, but typically can be from submicron thicknesses up to several millimeters in thickness.

The composition of the present disclosure, where utilized as a coating for a medical device, improves surface properties of the device such as, for example, cell and protein adhesion, lubricity, drug delivery, protein or DNA delivery, etc. The bioabsorbable blend coating may be especially useful in preventing bacterial adhesion/colonization, infection caused by or exacerbated by the device itself, and improving the handling properties of the device.

The composition of the present disclosure may also be formed into films and/or foams which, in turn, may be applied to wounds such as cuts, gashes, ulcers and burns to aid healing. Medicinal agents such as wound healing agents and antimicrobials may be incorporated to speed healing of damaged tissues. In this manner, various growth factors, antibiotics and antifungals can be incorporated into the bioabsorbable blend of the present disclosure.

Where medicinal agents are included in the bioabsorbable blend of the present disclosure, the composition of the present disclosure may be utilized as a drug delivery device to provide site-specific release of medicinal agents which may be immediate release, delayed release or sustained release. Immediate release systems provide a drug dose instantly. Delayed release systems provide repetitive intermittent dosings of drug. Sustained release systems achieve slow release of a drug over an extended period of time and should maintain a therapeutically effective concentration of drug at the target site. Medicinal agents that are mingled with the compositions herein typically provide delayed or sustained release therapy by diffusion from the bioabsorbable implant and/or bioabsorbable coating as it degrades.

The following examples are illustrative of specific embodiments of the polymeric compositions and should not be construed as limitations thereof.

Example 1

A biocompatible, biodegradable polymer was produced as follows. A one gallon reactor vessel was cleaned and subjected to a vacuum to reach a pressure of less than 1 Torr. 1000±1 grams of poloxamer 188 (PLURONIC® F68) was added to the one gallon reactor vessel, after which time a vacuum was again applied to obtain a pressure less than 1 Torr. The temperature was raised to about 105° C. and the PLURONIC® F68 was dried in the reactor for about 14 (±4) hours. During this time period, 1275±1 grams of ε-caprolactone was added to a 3 liter round bottom flask, and 225±1 grams of glycolide was added to a 500 ml round bottom flask. Between 75 and 90 minutes prior to the end of the drying of the PLURONIC® F68, the ε-caprolactone and glycolide were placed in an oven heated to a temperature of 105° C. After the drying of the PLURONIC® F68 was complete, the glycolide was added to the reactor, followed by the addition of the ε-caprolactone. The reactor was then backfilled with nitrogen, and then 295 µL of stannous octoate was added to the reactor as a catalyst.

The reactor was then heated to 178° C. (±3° C.), and the reaction was allowed to continue for 4.5 (±0.25) hours. After the reaction was complete, the polymerized bioabsorbable polymer was extruded and allowed to cool for a minimum of 16 hours.

The resulting bioabsorbable polymer was then subjected to an additional heat treatment. The bioabsorbable polymer was placed in a vacuum oven, which was heated to a temperature of 110° C. (±3° C.) in a vacuum at a pressure less than 1 Torr, for 30±2 hours. After heating, the polymer was allowed to cool under vacuum for a minimum of 6 hours.

NMR of the bioabsorbable polymer was conducted utilizing a Bruker AC300 NMR spectrometer. The proton spectra obtained had peaks which permitted the identification of the components of the bioabsorbable polymer.

The resulting bioabsorbable terpolymer was found to possess about 40% by weight PLURONIC® F68, about 51% by weight of caprolactoyl groups, about 9% by weight of glycoyl groups, and ≦1% by weight of residual caprolactone monomer.

Example 2

Monofilament surgical sutures which prevented the attachment and colonization of bacteria and provided enhanced suture handling characteristics, including reduced tissue drag, were prepared as follows. The polymer of Example 1 was solvated in methylene chloride at concentrations of 2, 5 and 10% (w/w). Monofilament polybutester (a copolymer of butylene terephthalate and polytetramethylene ether glycol) surgical sutures were coated by dip coating with each solution, to produce a uniform coating on the sutures. The resulting coating levels were 1.08%, 3.64% and 6.80% based on the weight of the suture for the 2%, 5% and 10% solutions, respectively. The coating from the 10% solution was found to prevent bacterial colonization of sutures at levels of clinical infection for at least 8 days. In contrast, other monofilaments, including uncoated polybutester sutures reached levels of clinical infection in as little as 3 days.

Example 3

Braided multifilaments made of a glycolide/lactide copolymer coated with a mixture of a caprolactone/glycolide copolymer and calcium stearoyl lactylate as described in the Examples of U.S. Pat. No. 5,716,376 (the disclosure of which is incorporated herein by this reference) were coated with the polymer of Example 1. The coating polymer was solvated in methylene chloride (2, 5 and 10% (w/w)) and the sutures coated with one of three solutions by dip coating. The additional coating polymer prevented bacterial adhesion and colonization in a more effective manner than observed with the uncoated sutures or with Ethicon's VICRYL® Plus suture (a suture made of a glycolide/lactide copolymer having a coating including triclosan).

Example 4

This bioabsorbable polymer of Example 1 was blended with the solution of Example 3 of U.S. Pat. No. 5,716,376 containing an ϵ-caprolactone/glycolide copolymer and calcium stearoyl lactylate represented about 2, 5 and 10% (w/w) of the resulting solution.

Multifilament braided glycolide/lactide surgical sutures were coated with the bioabsorbable blend by dip coating the suture in the solution having the bioabsorbable blend, and driving off the solvent by heating to produce a useable surgical suture.

Example 5

Varying amounts (2%, 5% and 10% w/w) of the bioabsorbable polymer of Example 1 were blended into the solution of Example 2 of U.S. Pat. No. 5,716,376 which was then modified by adding 2% triclosan. The resulting solutions were applied to multifilament, braided glycolide/lactide copolymer sutures.

The resulting suture having the coating of the bioabsorbable blend with triclosan and untreated sutures are tested for resistance to bacterial colonization using standard techniques. Generally, the sutures are exposed to *Escherichia coli* and the amount of bacteria growing on the suture is determined by counting the number of colony forming units. The results of these experiments are set forth in FIG. 1. As is apparent from FIG. 1, the suture having the coating of the bioabsorbable blend with triclosan prevented bacterial colonization on the suture material for up to 21 days, a marked improvement over the untreated suture. In addition, suture having the coating of the bioabsorbable blend with triclosan exhibited a large zone of inhibition (ZOI) of bacterial growth (approximately 20 mm).

Example 6

An anti-inflammatory coated surgical suture is prepared as follows. The bioabsorbable polymer of Example 1 of is solvated in methylene chloride at a concentration of 10% (w/w). Then, a 2% (w/w) salicylate solution is prepared in reverse osmosis (RO) water. Water/organic emulsions are prepared with the ratio of the bioabsorbable polymer solution:salicylate solution ranging from 8:2 to 2:8. Emulsions are formed under vigorous stirring and a surgical suture is coated with the bioabsorbable polymer and salicylate solution by dip coating techniques. The amount of the resulting coating ranges from 1-5% (w/w) of the base suture substrate. The polymer coating containing salicylate prevents bacterial colonization on the suture material for up to 14 days and exhibits a large zone of inhibition (ZOI) of bacterial growth (approximately 20 mm).

Example 7

Antimicrobial surgical suture coatings containing ionic silver and/or silver glass particles are prepared as follows. The bioabsorbable polymer of Example 1 is solvated in methylene chloride at concentration of 10% (w/w). Suspension/solutions of various silver salts (nitrate, citrate, sulfadiazine, lactate, etc.) are prepared in reverse osmosis (RO) water under high speed mixing. Water/organic emulsions are prepared with the ratio of the bioabsorbable polymer coating solution:silver suspension/solutions ranging from 8:2 to 2:8. Emulsions are formed under vigorous stirring and surgical sutures were coated by dip coating techniques. The coating is present in an amount from 0.5% to 15% (w/w) of the base suture substrate, preferably 1-5% (w/w). The polymer coating containing ionic silver prevents bacterial colonization on the suture material.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:
1. A blend comprising: a bioabsorbable terpolymer comprising from about 30 to about 50 weight percent of a polyoxyalkylene copolymer, from about 40 to about 50 weight percent epsilon-caprolactone, the balance of the copolymer comprising at least one other copolymerizable monomer selected from the group consisting of glycolide, lactide, p-dioxanone and trimethylene carbonate; and a polymer comprising two or more monomers selected from the group consisting of lactide, glycolide, lactic-acid, lactones, glycolic acid; carbonates, orthoesters, absorbable urethanes, absorbable nylons, polyethylene glycol-polypropylene glycol, polystyrene, n-vinyl pyrrolidine, n-vinyl pyridine, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorocholine.

2. The blend of claim 1 wherein the polymer comprises a copolymer of epsilon caprolactone and glycolide.

3. The blend of claim 1 further comprising a fatty acid component.

4. The blend of claim 3 wherein the fatty acid component comprises a salt of a $C_6$ or higher fatty acid.

5. The blend of claim 4 wherein the fatty acid salt is selected from the group consisting of calcium, magnesium, barium, aluminum, and zinc salts of $C_6$ or higher fatty acids.

6. The blend of claim 4 wherein the fatty acid salt comprises calcium stearate.

7. The blend of claim 3 wherein the fatty acid component comprises a salt of a fatty acid ester selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate.

8. The blend of claim 1 further comprising a wax.

9. The blend of claim 8 wherein the wax is selected from the group consisting of polyethylene wax, ethylene copolymer wax, halogenated hydrocarbon waxes, hydrogenated vegetable oil, beeswax, caranuba wax, paraffin, microcrystalline wax, candelillia, spermacetic wax, and mixtures thereof.

10. The blend of claim 1 further comprising a phospholipid.

11. The blend of claim 10 wherein the phospholipid is selected from the group consisting of phosphatidylcholine, mono-acyl phosphatidylcholine, diacyl phosphatidylcholine, phosphatidylserine, phosphatidylethanolamine, phosphatidylinositol, phosphatidylglycerol, plasmalogen, sphingomyelin, ceramide, ciliatin, and copolymers having phosphorylcholine groups.

12. The blend of claim 1 further comprising a medicinal agent.

13. The blend of claim 12 wherein the medicinal agent is selected from the group consisting of antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, proteins, nucleic acids, steroids, polysaccharides, and enzymes.

14. A medical device fabricated in whole or in part from the blend of claim 1.

15. A surgical suture coated with a composition comprising the blend of claim 1.

16. An emulsion comprising: a bioabsorbable terpolymer comprising about 30 to about 50 weight percent of a polyoxyalkylene copolymer, about 40 to about 50 weight percent epsilon-caprolactone, the balance of the copolymer comprising at least one other copolymerizable monomer selected from the group consisting of glycolide, lactide, p-dioxanone and trimethylene carbonate; and a polymer derived from two or more monomers selected from the group consisting of lactide, glycolide, lactic acid, lactones, glycolic acid, carbonates, orthoesters, absorbable urethanes, absorbable nylons, polyethylene glycol-polypropylene glycol, polystyrene, n-vinyl pyrrolidine, n-vinyl pyridine, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorocholine.

17. The emulsion of claim 16 wherein the polymer comprises a copolymer of epsilon caprolactone and glycolide.

18. The emulsion of claim 16 further comprising a fatty acid component.

19. The emulsion of claim 18 wherein the fatty acid component comprises a salt of a $C_6$ or higher fatty acid.

20. The emulsion of claim 19 wherein the fatty acid salt is selected from the group consisting of calcium, magnesium, barium, aluminum, and zinc salts of $C_6$ or higher fatty acids.

21. The emulsion of claim 19 wherein the fatty acid salt comprises calcium stearate.

22. The emulsion of claim 18 wherein the fatty acid component comprises a salt of a fatty acid ester selected from the group consisting of magnesium stearoyl lactylate, aluminum stearoyl lactylate, barium stearoyl lactylate, zinc stearoyl lactylate, calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, zinc olelyl lactylate and calcium stearoyl lactylate.

23. The blend of claim 16 further comprising a wax.

24. The blend of claim 23 wherein the wax is selected from the group consisting of polyethylene wax, ethylene copolymer wax, halogenated hydrocarbon waxes, hydrogenated vegetable oil, beeswax, caranuba wax, paraffin, microcrystalline wax, candelillia, spermacetic wax, and mixtures thereof.

25. The blend of claim 16 further comprising a phospholipid.

26. The blend of claim 25 wherein the phospholipid is selected from the group consisting of phosphatidylcholine, mono-acyl phosphatidylcholine, diacyl phosphatidylcholine, phosphatidylserine, phosphatidylethanolamine, phosphatidylinositol, phosphatidylglycerol, plasmalogen, sphingomyelin, ceramide, ciliatin, and copolymers having phosphorylcholine groups.

27. The emulsion of claim 16 further comprising a medicinal agent.

28. The emulsion of claim 27 wherein the medicinal agent is selected from the group consisting of antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, proteins, nucleic acids, steroids, polysaccharides, and enzymes.

29. A drug delivery device fabricated in whole or in part from the emulsion of claim 16.

30. A surgical suture coated with a composition comprising the emulsion of claim 16.

* * * * *